United States Patent
Hou et al.

(10) Patent No.: US 10,000,870 B2
(45) Date of Patent: Jun. 19, 2018

(54) CONDUCTIVE LINE STITCHING METHOD

(71) Applicant: KING'S METAL FIBER TECHNOLOGIES CO., LTD., Taichung (TW)

(72) Inventors: Jaang Jiun Hou, Taipei (TW); Yu Hsun Kang, Taipei (TW); Reng Sho Chen, Taipei (TW); Shu Fen Liao, Taipei (TW); Hao Chen Wang, Taipei (TW); Heng Te Chou, Taipei (TW)

(73) Assignee: KING'S METAL FIBER TECHNOLOGIES CO., LTD., Taichung (TW)

( * ) Notice: Subject to any disclaimer, the term of this patent is extended or adjusted under 35 U.S.C. 154(b) by 9 days.

(21) Appl. No.: 15/210,311

(22) Filed: Jul. 14, 2016

(65) Prior Publication Data

US 2017/0342618 A1     Nov. 30, 2017

(30) Foreign Application Priority Data

May 30, 2016   (TW) .............................. 105116942 A

(51) Int. Cl.
   *D05B 23/00*   (2006.01)
   *A61B 5/0408*   (2006.01)
   *A61B 5/00*   (2006.01)

(52) U.S. Cl.
   CPC .......... *D05B 23/00* (2013.01); *A61B 5/0408* (2013.01); *A61B 5/6805* (2013.01); *A61B 2562/125* (2013.01); *D05D 2303/40* (2013.01)

(58) Field of Classification Search
   CPC ........ D05B 17/00; D05B 93/02; D05B 93/00; A61B 5/04085; A61B 5/02055; A61B 5/0006; A61B 5/6802
   USPC .................................. 112/475.21, 475.26
   See application file for complete search history.

(56) References Cited

U.S. PATENT DOCUMENTS

| | | | | |
|---|---|---|---|---|
| 5,950,553 A | * | 9/1999 | Bohlinger | D05B 35/064 112/436 |
| 6,668,380 B2 | * | 12/2003 | Marmaropoulos | A61N 1/0484 2/69 |
| 7,395,106 B2 | * | 7/2008 | Ryu | A61B 5/04085 600/388 |
| 7,783,334 B2 | * | 8/2010 | Nam | A61B 5/04085 600/388 |
| 8,308,489 B2 | * | 11/2012 | Lee | H01R 13/2407 2/69 |
| 8,909,318 B2 | * | 12/2014 | Nordstrom | A61B 5/0006 600/388 |
| 9,282,893 B2 | * | 3/2016 | Longinotti-Buitoni | A61B 5/02055 |
| 9,629,584 B2 | * | 4/2017 | Macia Barber | A61B 5/04085 |
| 2005/0054941 A1 | * | 3/2005 | Ting | A61B 5/0408 600/529 |

(Continued)

*Primary Examiner* — Danny Worrell
(74) *Attorney, Agent, or Firm* — Rabin & Berdo, P.C.

(57) ABSTRACT

A conductive line stitching method is disclosed, wherein a metal line is arranged in a protection layer to form a conductive line, which is subjected to the steps of forming conductive line, laying cloth, performing stitching, combining a device, and connecting conductive line to have the conductive line located in a stitching area to carry out a subsequent operation for connection with a device, thereby achieving an effect of being processed with a one-time process and concealing the conductive line facilitated on smart clothes.

16 Claims, 17 Drawing Sheets

(56) References Cited

U.S. PATENT DOCUMENTS

2014/0238151 A1\* 8/2014 Dunne .................. D05B 97/12
　　　　　　　　　　　　　　　　　　　　　　　73/862.474
2015/0168238 A1\* 6/2015 Raut .................... G01N 27/048
　　　　　　　　　　　　　　　　　　　　　　　702/42

\* cited by examiner

CONDUCTIVE LINE STITCHING METHOD

BACKGROUND OF THE INVENTION

1. Field of the Invention

The present invention generally relates to a conductive line stitching method, and more particularly to one that includes the steps of forming conductive line, laying cloth, performing stitching, combining device, and connecting conductive line to have a conductive line located on stitching area to facilitate a subsequent processing operation of combination with a device, thereby being applicable to clothing of all sort of clothes and outwears.

2. Description of Related Art

Recently, smart clothing is getting popular. The smart clothing focused by all major manufacturers is one that involves an electronic device which is capable of detecting physiological signals and is mounted in the clothing so that when the clothing is worn, detection of the physiological signal can be performed. Further, the smart clothing is provided therein with conductive lines in order to transmit the physiological signal detected by the electronic device and also to transmit electrical power.

However, the conductive lines mounted in the smart clothing was attached to a surface layer of the clothing by means of adhesive plastic films or was coupled inside the clothing through hemming so that the conductive line was perceived as a projection for the human skin and may impress the skin to form impressing marks which made it uncomfortable for skin.

Further, both adhesive plastic films and hemming require additional processing to be carried out and it was not possible to have the conductive line combined with the smart clothing in one-time sewing job.

Thus, in view of the above problems, for the purpose of providing a conductive line stitching method that allows for one-time sewing operation and helps conceal the conductive line, the present inventor has been devoted himself to study and design in order to provide such a stitching method used by the public. This is the motivation of creation of the present invention.

SUMMARY OF THE INVENTION

The primary object of the present invention is to provide a conductive line stitching method, in which a metal line is arranged in a protection layer to form a conductive line transmitting detected physiological signal, which is subjected to the following steps of forming conductive line, laying cloth, performing stitching, combining device, and connecting conductive line, to have the conductive line located on stitching area to facilitate a subsequent operation of combination with an electrical detecting device, thereby providing the effects of allowing for one-time sewing operation and concealing the conductive line so as to improve overall utilization.

A secondary object of the present invention is to provide a conductive line stitching method, in which a conductive line is positioned on stitching area of two cloth sheets that are stacked on each other, stitching is then performed on the stitching area of the two stacked cloth sheets to have the conductive line located inside the stitching line so stitched thereby allowing the conductive line to be concealed along the stitching line and thus improving comfortableness and aesthetics of wearing so as to improve overall utilization.

A further object of the present invention is to provide a conductive line stitching method, in which two cloth sheets are stacked such that stitching area is exposed and then stitching area of the two stacked cloth sheets are stitched with a conductive line which is directly used as a stitching line for stitching the stitching area, both allowing the stitching area to be stitched and also connection through the conductive line with an electrical detecting device for transmission of data, thereby making the conductive line multi-functional so as to improve overall stitching utilization.

To achieve the above objects, the present invention is a conductive line stitching method, in which a first method comprises the following steps: forming conductive line: wherein a metal line is arranged in a protection layer to form a conductive line; laying cloth: wherein the conductive line is positioned on stitching area of two stacked cloth sheets; performing stitching: wherein stitching is performed on the stitching area of the stacked cloth sheets to have the conductive line located inside the stitching line; combining device: wherein a device is combined to the stitching line so stitched; and connecting conductive line: wherein the device is set to connect with the conductive line contained in the stitching line to allow the device to conduct transmission of detected the physiological signal through the conductive line.

A second method comprises the following steps: forming conductive line: wherein a metal line is arranged in a protection layer to form a conductive line; laying cloth: wherein two cloth sheets are stacked such that stitching area is exposed; performing stitching: wherein the stitching area of the two stacked cloth sheets are stitched with the conductive line; combining device: wherein a device is combined to the conductive line so stitched; and connecting conductive line: wherein the device is set to connect with the conductive line so stitched to allow the device to conduct transmission of detected the physiological signal through the conductive line.

Other features and embodiments of the present invention will be explained by the following detailed description with reference to the attached drawings for further understanding.

DETAILED DESCRIPTION OF THE PREFERRED EMBODIMENTS

Referring to FIGS. 1-17, which illustrate schematic views of the present invention, a preferred embodiment of a conductive line stitching method according to the present invention is applicable on clothing, such as various clothes and outwears. The present invention is different from conventional conductive line processing methods and application in the manufacturing process nowadays, and processes efficiently with one single process and concealing conductive line. Further, in addition to the efficiency, other advantages of improving wearing comfortableness and aesthetics are also achieved. Thus, the present inventor studies and improves the manufacturing process of stitching a conductive line. The following is a description for illustrating a first type and a second type of conductive line stitching method according to the present invention.

Figure 1:
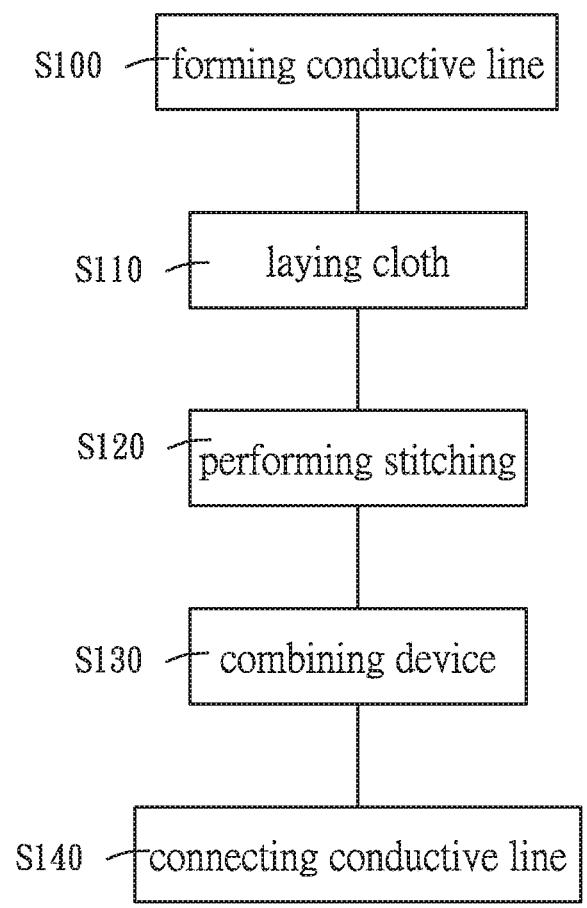
FIG. 1 is a flow chart illustrating major steps of a first method according to the present invention.
Figure 4:
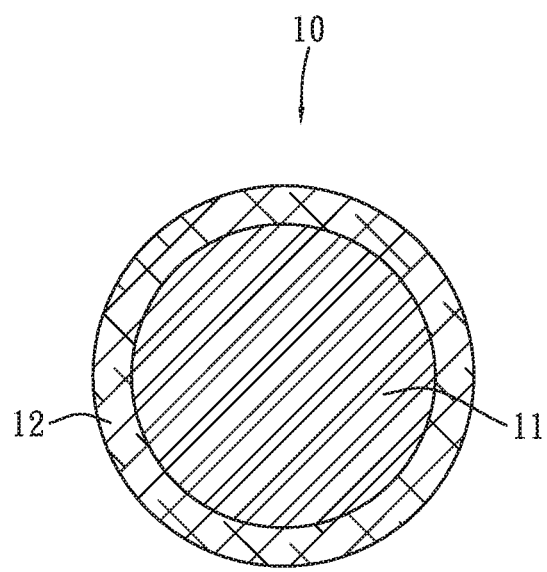
FIG. 4 is a cross-sectional view showing a conductive line adopted in the first method of the present invention.

In the first type of conductive line stitching method (as shown in FIG. 1), a step to be first performed is forming conductive line S100: wherein a metal line is arranged inside a protection layer to form a conductive line; and the conductive line 10 is generally formed by having a metal line 11 enclosed and covered with an outside protection layer 12 (as shown in FIG. 4) in order to prevent the metal line 11 from being directly exposed to exterior environment, and the metal line 11 can be a copper wire or a gold wire or wires made of other metals. The external protection layer 12 can be an insulation layer formed of a material comprising polyvinyl chloride (PVC) or the likes, or can alternatively be a yarn line formed by spinning cotton, silk, hemp, animal hairs, or artificial fibers and a winding process is adopted to wind the yarn line around and covering the outside of the metal line 11. After the completion of the above step of forming conductive line S100, the next step is performed.

Figure 5:
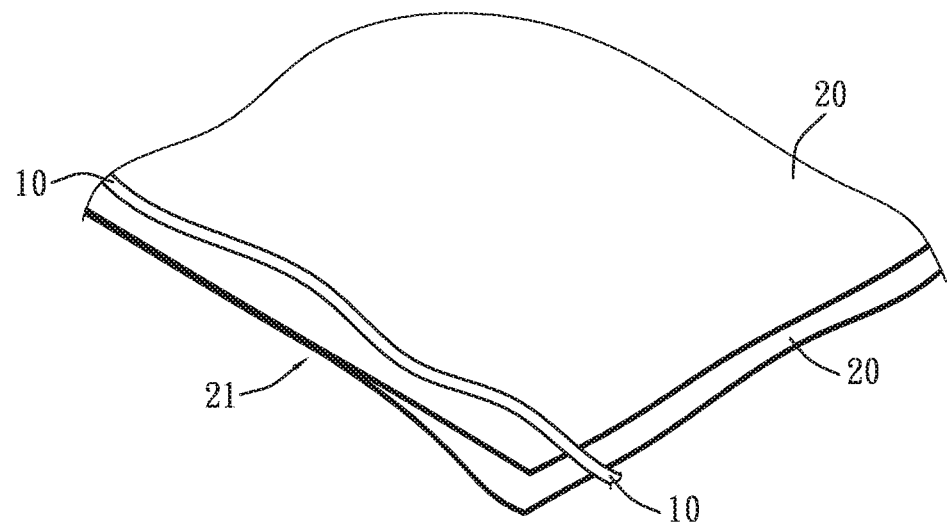
FIG. 5 is a schematic view showing the conductive line laid on cloth sheets adopted in the first method of the present invention.

Further, the next step to perform is laying cloth S110: wherein the conductive line is positioned on stitching area 21 of two cloth sheets that are stacked on each other; and generally, the above-described conductive line 10 is laid on the stitching area 21 of the two stacked cloth sheets 20 on which a stitching operation is to be performed (as shown in FIG. 5), where the stitching area 21 are stitching edges of the cloth sheets 20 on which stitching is to be implemented. After the completion of the said step of laying cloth S110, the next step is performed.

Figure 6:
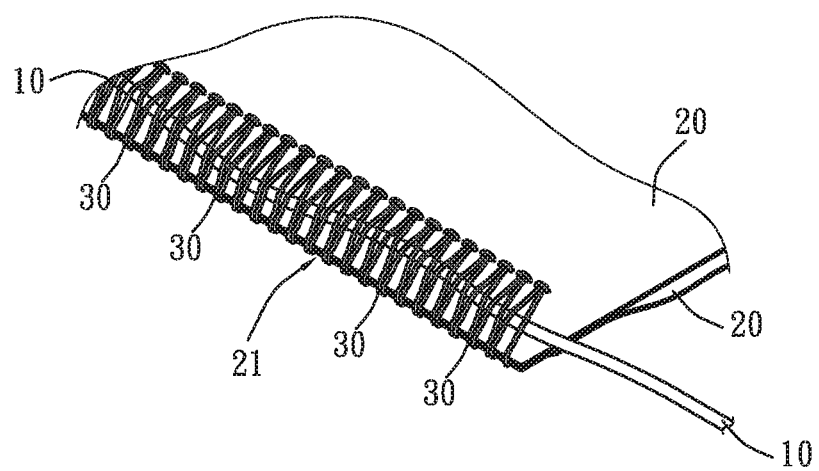
FIG. 6 is a schematic view showing stitching the conductive line and the cloth sheets adopted in the first method of the present invention.

Further, the next step to perform is performing stitching S120: wherein the stitching area 21 of the two stacked cloth sheets 20 are subjected to stitching such that the conductive line 10 is located inside the stitching line; and the two stacked cloth sheets 20 and the conductive line 10 positioned on the stitching area 21 of the two cloth sheets 20 are stitched together (as shown in FIG. 6), wherein the stitching can be performed in a manner of overlock, cover stitch, flat-locking, and lock stitch or manually stitching, and the said performing stitching can have the conductive line 10 stitched together so that the conductive line 10 is located inside the stitching line 30 in such a stitched manner to allow the conductive line 10 to be fixed by the stitching line 30 on the stitching area 21 of the two cloth sheets 20. After the completion of the said step of performing stitching S120, the next step is performed.

Figure 7:
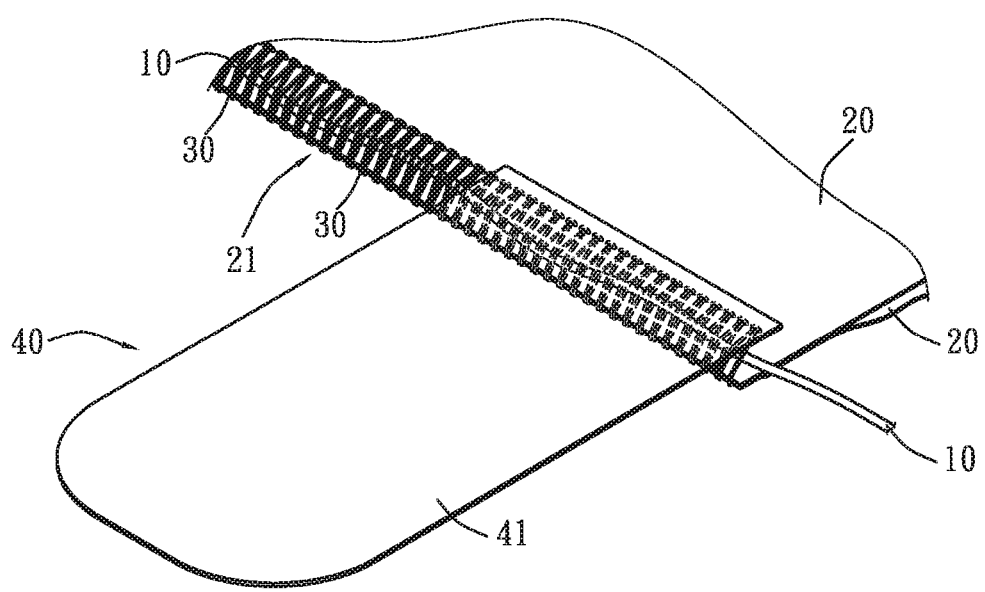
FIG. 7 is a schematic view showing the conductive line being coupled with the electrode plate adopted in the first method of the present invention.
Figure 8:
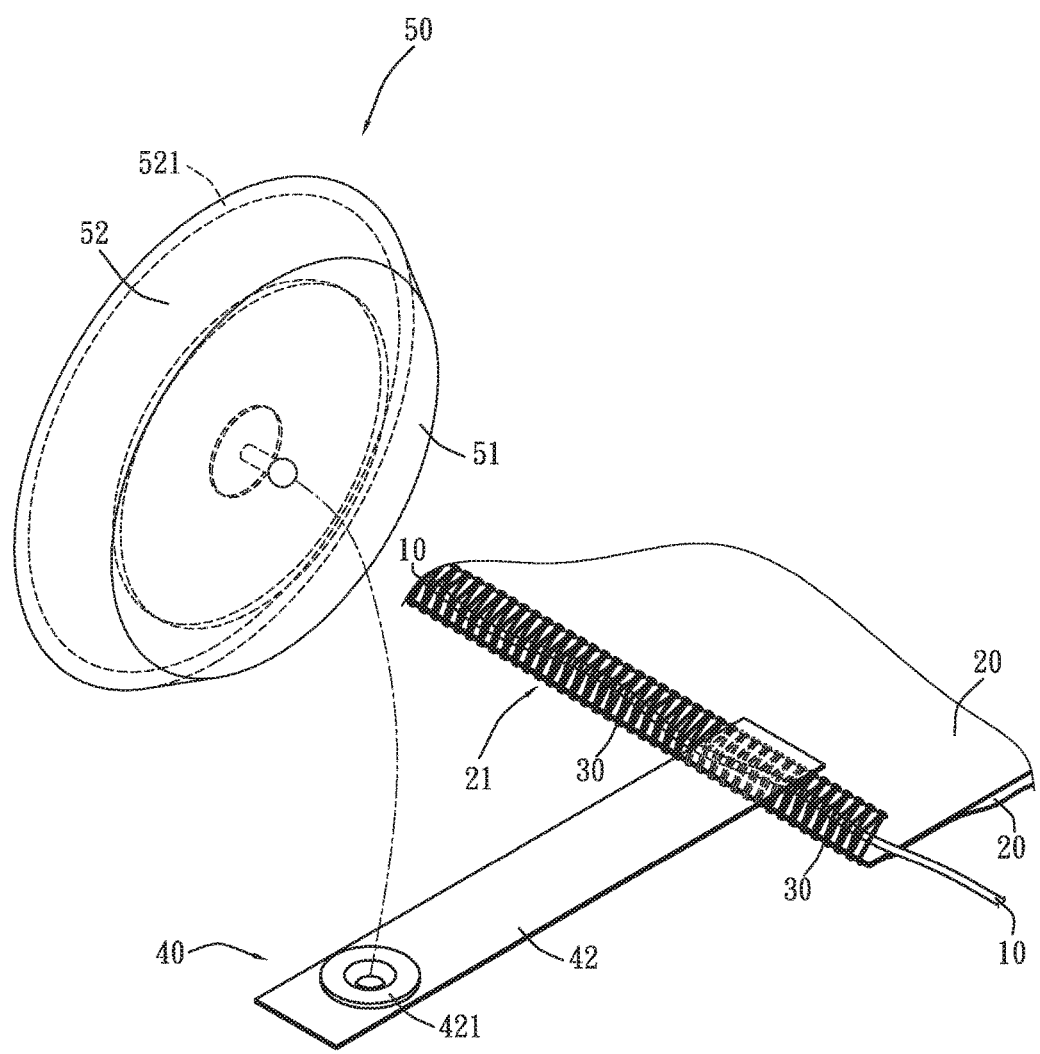
FIG. 8 is a schematic view showing the conductive line being connected with a suction-cup electrode adopted in the first method of the present invention.
Figure 9:
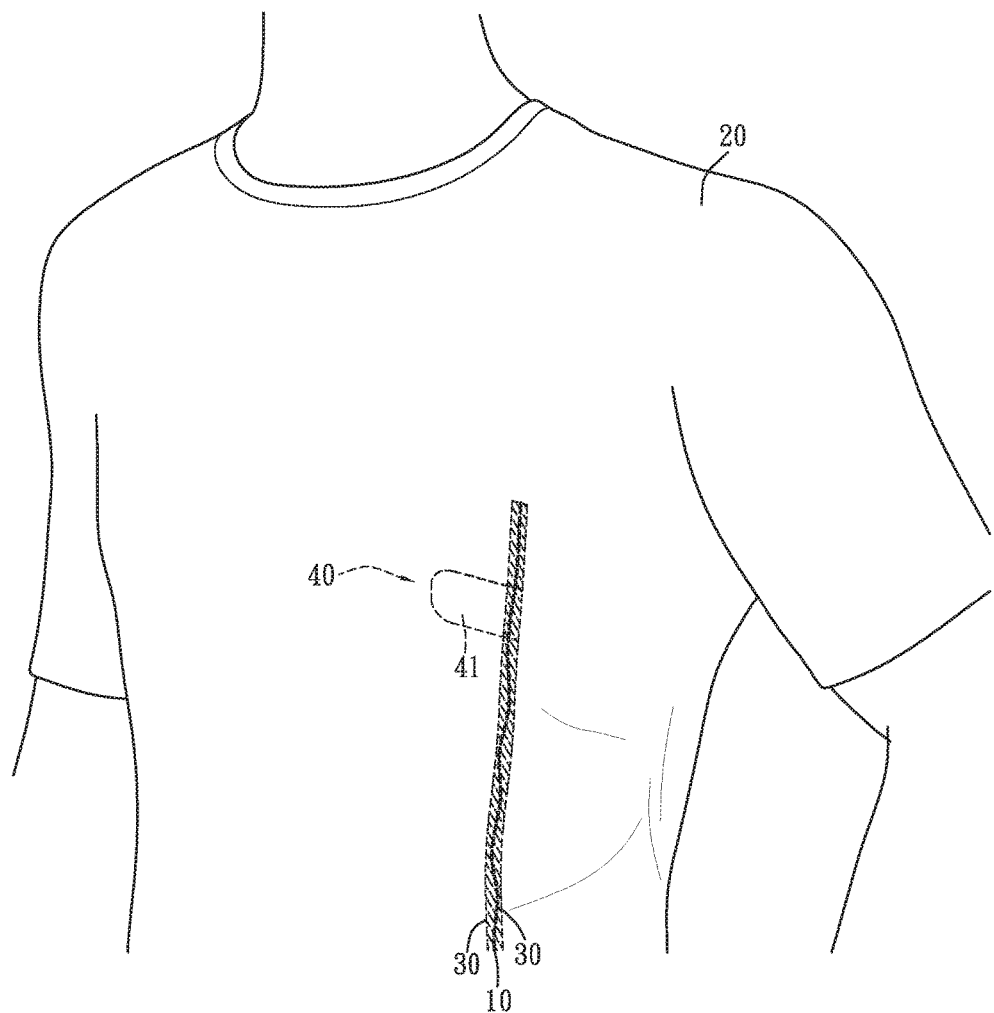
FIG. 9 is a schematic view showing sewing the electrode plate on clothing adopted in the first method of the present invention.

Further, the next step to perform is combining device S130: wherein the stitching line 10 so stitched is combined with a device which conducts transmission of detected the physiological signal; and the stitching area 21 of the two cloth sheets 20 stitched in such a manner comprises a conductive line 10 thereon and the conductive line 10, and provides an effect of transmission of detected physiological signal and/or data and may thus be connectable to a device 40 that requires data transmission (as shown in FIG. 7 or 8), where the device 40 can be an electrode plate 41, a conductive piece 42, or any other object capable of detection or data transmission. After the completion of the said combining device S130, the next step is performed.

When the device, involved in the above-described step of combining device S130, is an electrode plate 41, then two types of combining step can be adopted, wherein the electrode plate 41 is capable of detecting a physiological signal of a human body surface and the electrode plate 41 is formed of a plurality of non-conductive fiber yarns and a plurality of conductive fiber yarns woven or knitted together, or alternatively, the entirety is formed by weaving or knitting a plurality of conductive fiber yarns, and the electrode plate 41 is fixed stably on the human skin to carry out detection of a physiological signal. The above-mentioned physiological signal can be any one of body temperature, heartbeat, pulse, and breath. The first alternative type of the combining step (as shown in FIG. 2) is press-fusion S13010: wherein the electrode plate 41 and the conductive line 10 located in the stitching line 30 are press-jointed by a manner of ultrasonic wave so that the electrode plate 41 and the conductive line 10 are fused and connected; and, in other words, one end of the electrode plate 41 is positioned at the stitching line 30 in which the conductive line 10 is included and a machine is operated to generate instantaneous high thermal energy by means of ultrasonic wave for conducting press-jointing on the electrode plate 41, the stitching line 30, and the conductive line 10 simultaneously (as shown in FIG. 7), allowing the protection layer 12 of the conductive line 10 located in the stitching line 30 to get melted due to the instantaneous high thermal energy and thus expose the internal metal line 11, and allowing the exposed metal line 11 to form a fusion-connected condition with respect to the electrode plate 41 thereby forming polarity engagement.

Figure 2:
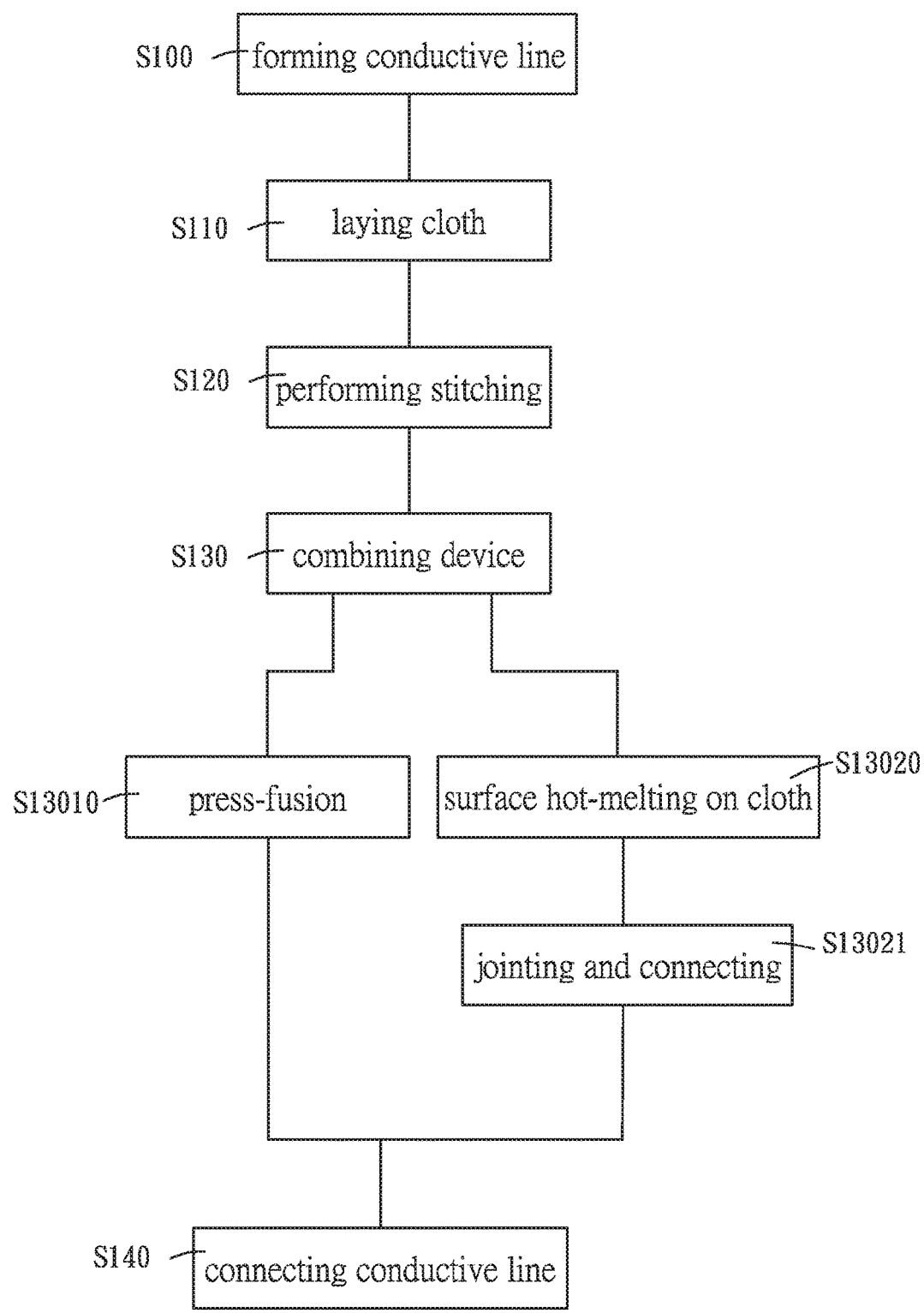
FIG. 2 is a flow chart illustrating the first method of the present invention that adopts an electrode plate.

Further, the second type of combining step (as shown in FIG. 2) is surface hot-melting on cloth S13020: wherein a section of the conductive line 10 located in the stitching line 30 is subjected to hot melting to expose the metal line on the surface of cloth sheet 20; and a site where a section of the conductive line 10 located inside the stitching line 30 is selected for removing the external protection layer 12 to expose the internal metal line 11, and then a machine (such as a hot melting gun) that could generate instantaneous high temperature is used to have the section that is selected to have the protection layer 12 removed (not shown). After the completion of the above-described surface hot-melting on cloth S13020, the next step will be performed is jointing and connecting S13021: wherein the electrode plate 41 is attached to or sewn to the location of the conductive line 10 where the metal line 11 is exposed to have the electrode plate 41 forming connection with the conductive line 10; and then, in the specific section where the protection layer 12 is removed from the conductive line 10, the electrode plate 41 is coupled to the stitching line 30 by means of attaching or sewing (not shown) to have the electrode plate 41 forming electrical connection with the conductive line 10 of which the protection layer 12 is removed and the metal line 11 is exposed.

Figure 3:
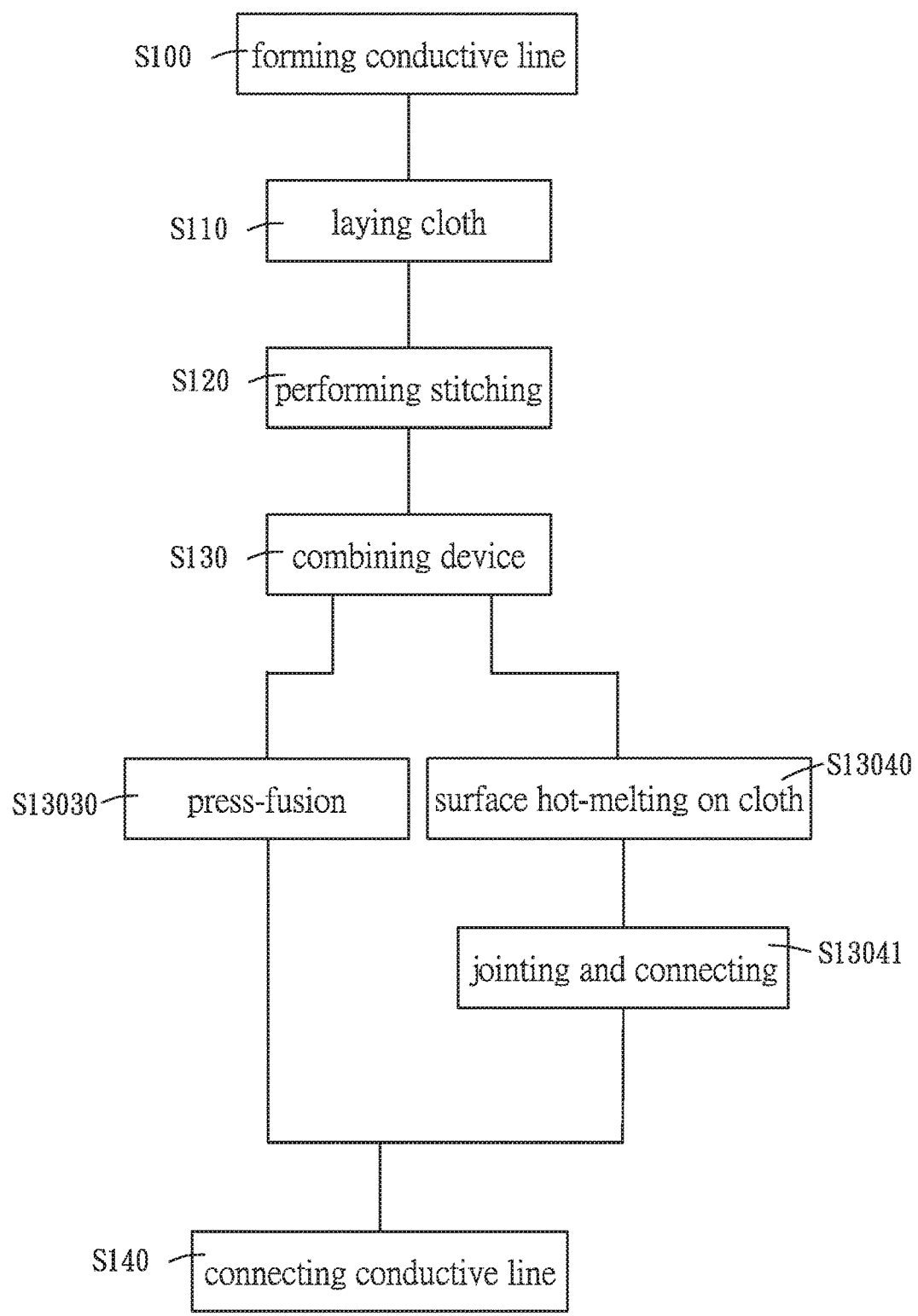
FIG. 3 is a flow chart illustrating the first method of the present invention that adopts a conductive piece.

Further, when the device 40 involved in the above-described step of combining device S130 is a conductive piece 42, two types of combining step are involved, wherein the conductive piece 42 comprises one of metal non-woven fabric, conductive rubber, conductive silicon rubber, and conductive films and possesses excellent performance of transmission of data or power through metallic material or conductive material contained therein. The first type of the combining step (as shown in FIG. 3) is press-fusion S13030: wherein the conductive piece 42 and the conductive line 10 located inside the stitching line 30 are press-jointed by a manner of ultrasonic wave so that the conductive piece 42 and the conductive line 10 are fused and connected; and, in other words, one end of the conductive piece 42 is positioned at the stitching line 30 in which the conductive line 10 is therefore coupled with and a machine is operated to generate instantaneous high thermal energy by means of ultrasonic wave for conducting press-jointing on the conductive piece 42, the stitching line 30, and the conductive line 10 simultaneously (as shown in FIG. 8), allowing the protection layer 12 of the conductive line 10 located inside the stitching line 30 to get melted due to the instantaneous high thermal energy and thus expose the internal metal line 11, and allowing the exposed metal line 11 to form a fusion-connected condition with respect to the conductive piece 42 thereby forming polarity engagement. The above-described conductive piece 42 that is fusion-connected to the conductive line 10 is provided with a connection portion 421, and the connection portion 421 is connectable with a suction-cup electrode 50 (as shown in FIG. 8), wherein the connection portion 421 and the suction-cup electrode 50 are respectively provided with mating male and female buckles or other applicable connection measures to allow the suction-cup electrode 50 to achieve a connected condition with the conductive piece 42 and the conductive line 10 via the connection portion 421. The suction-cup electrode 50 comprises a bottom portion 51, and the bottom portion 51, having an outer rim edge, which extends a circular part 52. Further, the circular part 52 has an upper end that forms an engagement surface 521 for being positionable and attached to a human body skin to carry out detection of a physiological signal. The above-mentioned physiological signal can be any one of body temperature, heartbeat, pulse, and breath.

Further, the second type of combining step (as shown in FIG. 3) is surface hot-melting on cloth S13040: wherein a section of the conductive line 10 located inside the stitching line 30 is subjected to hot melting to expose the metal line 11; that is, a section of the conductive line 10 located inside the stitching line 30 so stitched is selected for removing the external protection layer 12 and exposing the internal metal line 11 and a machine (such as a hot melting gun) that could generate instantaneous high temperature is used to have that section selected to remove the protection layer 12 by melting (not shown). After the completion of the above-described surface hot-melting on cloth S13040, the next step performed is jointing and connecting S13041: wherein the conductive piece 42 is attached to or sewn to the location of the conductive line 10 where the metal line 11 is exposed to have the conductive piece 42 forming connection with the conductive line 10; and then, the protection layer 12 is removed from the conductive line 10 and the conductive piece 42 is coupled to the stitching line 30 by means of attaching or sewing to have the conductive piece 42 forming electrical connection with the conductive line 10 of which the protection layer 12 is removed and the metal line 11 is exposed (not shown). The above-described conductive piece 42, fusion-connected to the conductive line 10, is provided with a connection portion 421, and the said connection portion 421 is connectable with a suction-cup electrode 50, wherein the connection portion 421 and the suction-cup electrode 50 are respectively provided with mating male and female buckles or other applicable connection measures to allow the suction-cup electrode 50 achieve a connected condition with the conductive piece 42 and the conductive line 10 through the connection portion 421. The suction-cup electrode 50 comprises a bottom portion 51, having an outer rim edge, which extends a circular part 52. Further, the circular part 52 has an upper end that forms an engagement surface 521 for being positionable and attached to a human body skin to carry out detection of a physiological signal. The above-mentioned physiological signal can be any one of body temperature, heartbeat, pulse, and breath.

Further, after the completion of the above-described step of combining device S130, the next step performed (as shown in FIGS. 1, 2, and 3) is connecting conductive line S140: wherein the device 40 is set in connection with the conductive line 10 located inside the stitching line 30 to allow the device 40 to conduct transmission through the conductive line 10; and the device 40 (whether being an electrode plate 41 or a conductive piece 42) forms electrical connection with the conductive line 10 inside the stitching line 30 by means of the above-described method so that the conductive line 10 may transmit signals and data detected by the device 40 to an electronic apparatus (such as a smart phone, a smart tablet computer, a notebook computer, a desktop computer, and medical equipment) or cloud (not shown) for interpreting the result of data to take preventive medical treatment in advance.

Figure 10:
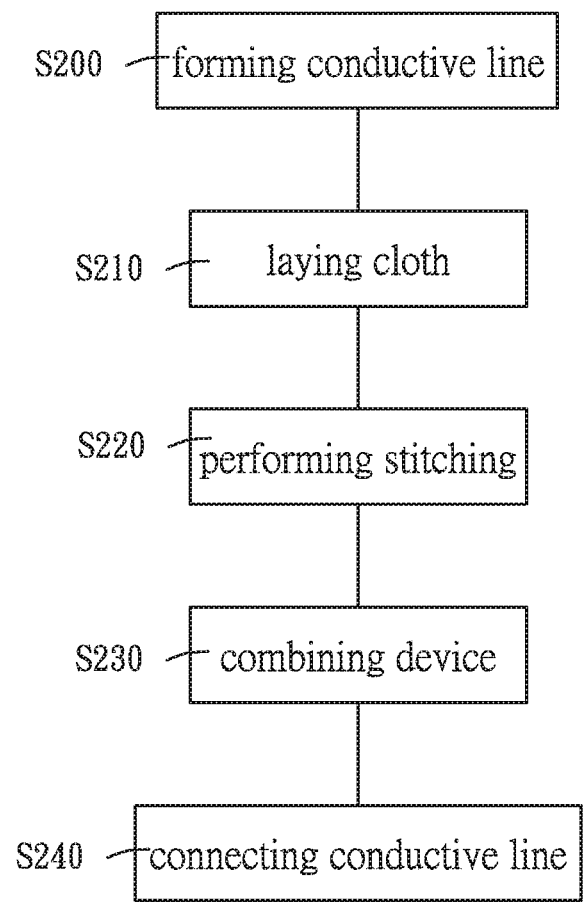
FIG. 10 is a flow chart illustrating major steps of a second method according to the present invention.
Figure 13:
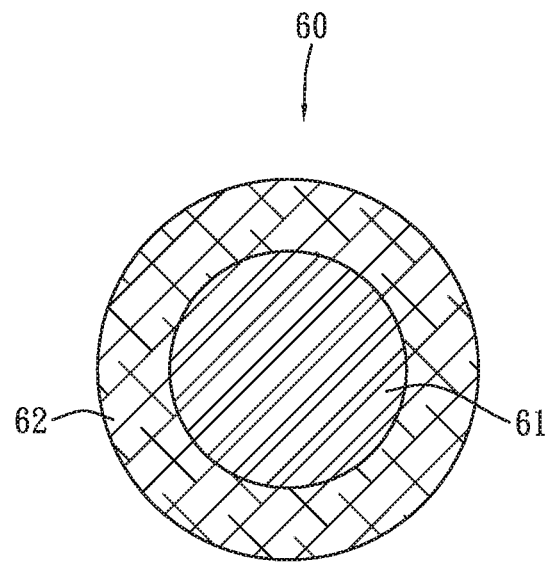
FIG. 13 is a cross-sectional view showing a conductive line adopted in the second method of the present invention.

Further, in the second embodiment of conductive line stitching method (as shown in FIG. 10), the first step to be performed is forming conductive line S200: wherein a metal line 61 is arranged inside a protection layer 62 to form a conductive line 60; and the conductive line 60 is primarily formed by a metal line 61 which is outside enclosed and covered with a protection layer 62 (as shown in FIG. 13) to prevent the metal line 61 from being directly exposed to exterior environment, meanwhile, the metal line 61 can be a copper wire or a gold wire or wires made of other metals. The external protection layer 12 can be an insulation layer formed of a material comprising polyvinyl chloride (PVC) or the likes, or can alternatively be a yarn line formed by spinning cotton, silk, hemp, animal hairs, or artificial fibers and a winding process is adopted to wind the yarn line around and cover the outside of the metal line 61. After the completion of the above forming conductive line S200, the next step is performed.

Further, the next step to perform is laying cloth S210: wherein the stitching area 71 of two stacked cloth sheets 70 are exposed; and generally, two to-be stitched cloth sheets 70 are stacked, and stitching is carried out at the stitching area 71, which is stitching edges of the cloth sheets 70 and stitching is to be implemented. After the completion of the above laying cloth S210, the next step is performed.

Figure 14:
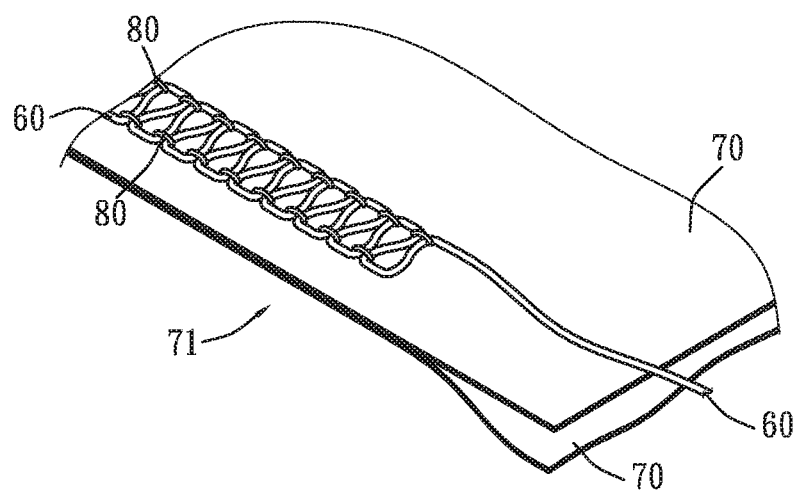
FIG. 14 is a schematic view showing stitching a conductive line and cloth sheets adopted in the second method of the present invention.

Further, the next step to be carried out is performing stitching S220: wherein the stitching area 71 of the two stacked cloth sheets 70 are subjected to be stitched with a conductive line 60; and in other words, the stitching area 71 of the two stacked cloth sheets 70 in the above-described step of laying cloth S210 is stitched by using a conductive line 60 directly (as shown in FIG. 14). A primary difference between this method and the first embodiment of conductive line stitching method lies in this step, wherein the conductive line 60 is used directly as a stitching line and a manual operation is applied to extend the conductive line 60 through a needle such that the stitching needle can be used directly to perform a stitching operation (not shown), or alternatively, the conductive line 60 is first installed in a sewing machine to be used in combination with other stitching line (yarn) 80 to carry out a stitching operation. The stitching can be performed in a manner of overlock, cover stitch, flatlocking, and lock stitch to have the conductive line 60 directly fixed at the stitching area 71 of the two stacked cloth sheets 70. After the completion of the above performing stitching S220, the next step is performed.

Figure 15:
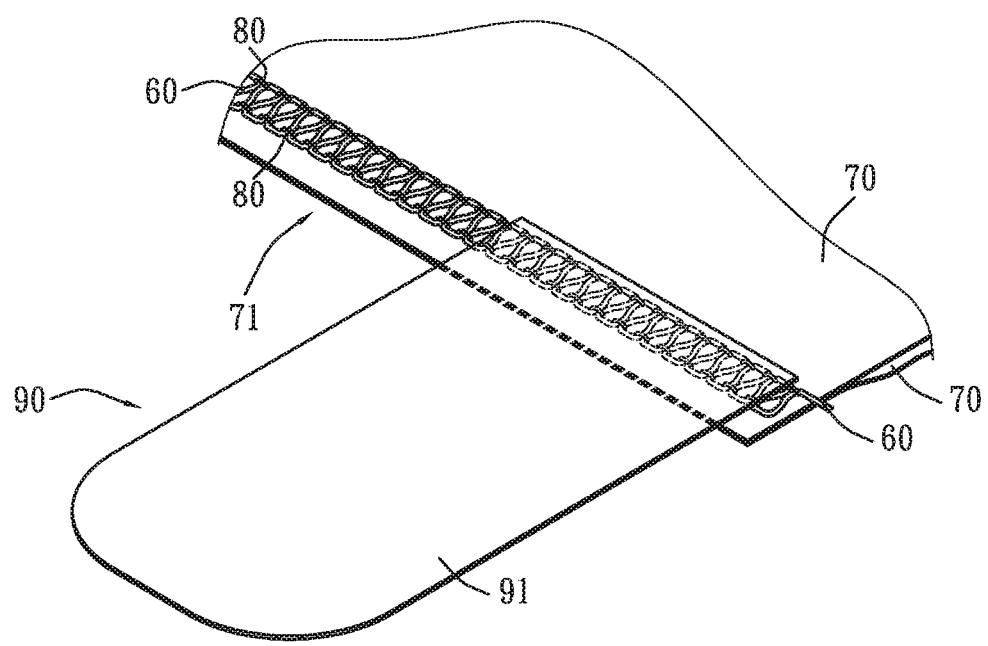
FIG. 15 is a schematic view showing the conductive line being coupled with the electrode plate adopted in the second method of the present invention.
Figure 16:
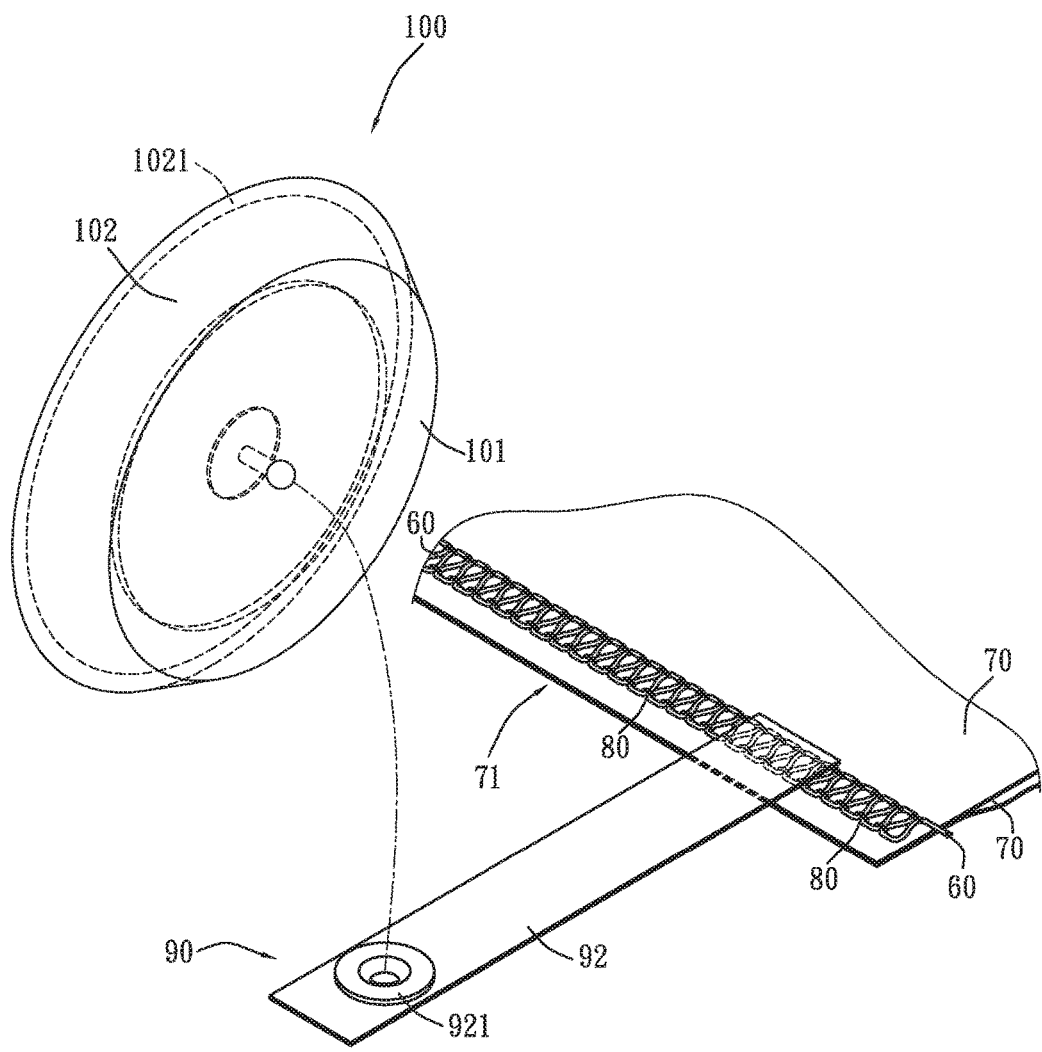
FIG. 16 is a schematic view showing the conductive line being connected with a suction-cup electrode adopted in the second method of the present invention.
Figure 17:
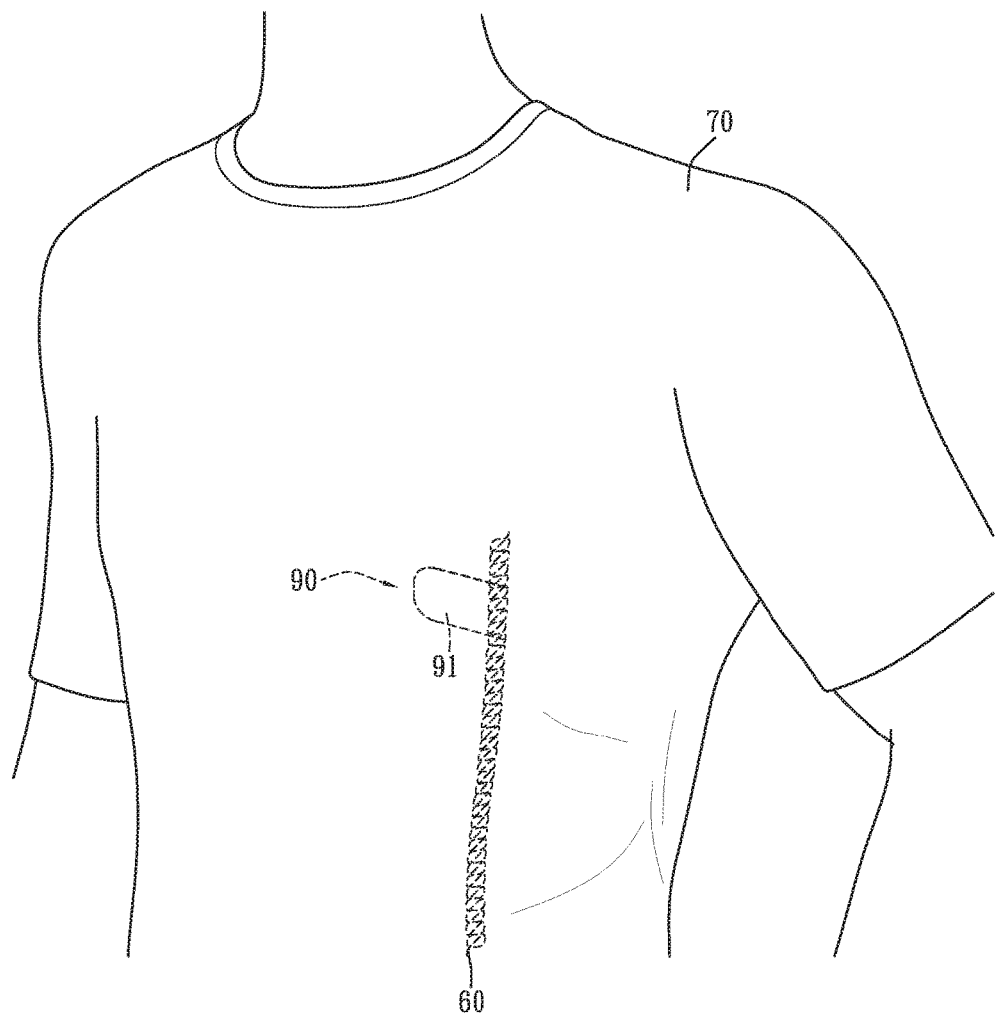
FIG. 17 is a schematic view showing sewing the electrode plate on clothing adopted in the second method of the present invention.

Further, the next step to perform is combining device S230: wherein the conductive line 60 stitched by such a manner is combined with a device 90; the stitching area 71 of the two stacked cloth sheets 70 comprises a conductive line 60 thereon and the said conductive line 60 provides an effect of transmission of data and may thus be connectable to a device 90 that requires data transmission (as shown in FIGS. 15 and 16), where the device 90 can be an electrode plate 91, a conductive piece 92, or any other object capable of detection or data transmission. After the completion of the above combining device S230, the next step is performed.

When the device involved in the above-described step of combining device S230 is an electrode plate 91, two types of combining step can be applied, wherein the electrode plate 91 is capable of detecting a physiological signal from a human body skin surface, or the electrode plate 91 is formed of a plurality of non-conductive fiber yarns and a plurality of conductive fiber yarns woven or knitted together, or alternatively, the entirety thereof is formed by weaving or knitting a plurality of conductive fiber yarns; and the electrode plate 91 is stably fixing on the human skin to carry out detection of a physiological signal. The above-mentioned physiological signal can be any one of body temperature, heartbeat, pulse, and breath. The first type of the combining step (as shown in FIG. 11) is press-fusion S23010: wherein the electrode plate 91 and the conductive line 60 so stitched are press-jointed by a manner of ultrasonic wave that the electrode plate 91 and the conductive line 60 are fused and connected; and, in other words, one end of the electrode plate 91 is fixed and stitched on the conductive line 60 (as shown in FIG. 15), and a machine is operated to generate instantaneous high thermal energy by means of ultrasonic wave for conducting press-jointing on the electrode plate 91 and the conductive line 60 simultaneously, which allows the protection layer 62 of the conductive line 60 located on the stitching area 71 to get melted due to the instantaneous high thermal energy and thus expose the internal metal line 61, and enables the exposed metal line 61 to form a fusion-connected condition with respect to the electrode plate 91 forming polarity engagement therefore.

Figure 11:
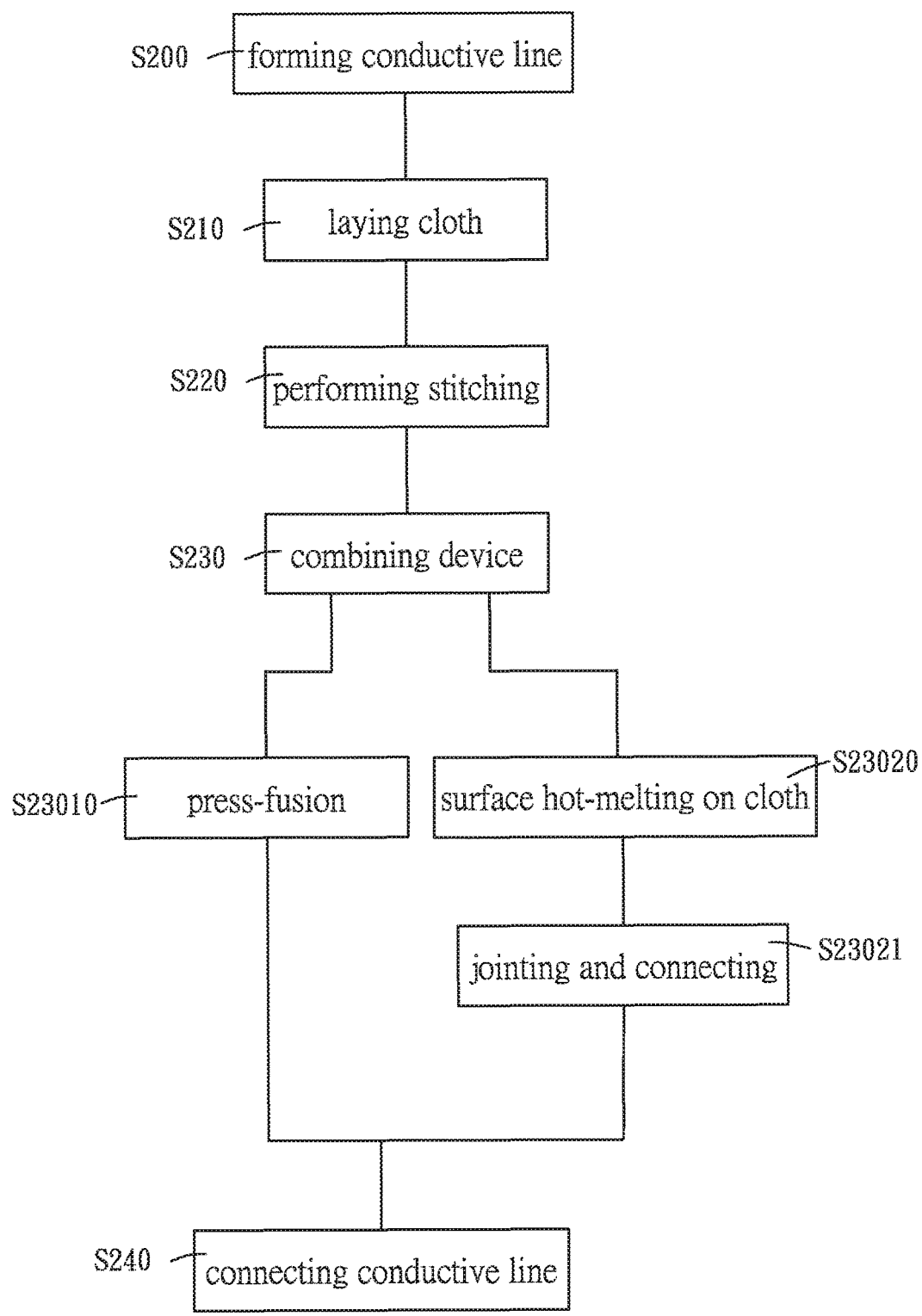
FIG. 11 is a flow chart illustrating the second method of the present invention that adopts an electrode plate.

Further, the second type of combining step (as shown in FIG. 11) is surface hot-melting on cloth 523020: wherein a section of the conductive line so stitched is subjected to hot melting to expose the metal line 61; and a section (not shown) of the stitched conductive line 60 is selected for removing the external protection layer 62 and exposing the internal metal line 61, and a machine (such as a hot melting gun) that could generate instantaneous high temperature is adopted to have the selected section to have the protection layer 62 removed by melting. After the completion of the above-described hot-melting and exposing 523020, the next step to perform is jointing and connecting 523021: wherein the electrode plate 91 is attached to or sewn to the location of the conductive line 60 where the metal line 61 is exposed to have the electrode plate 91 forming connection with the conductive line 60; and then, in the selected section where the protection layer 62 is removed from the conductive line 60, the electrode plate 91 is coupled to the conductive line 60 by means of attaching or sewing (not shown) to form electrical connection with the conductive line 60 of which the protection layer 62 is removed and the metal line 61 is exposed.

Figure 12:
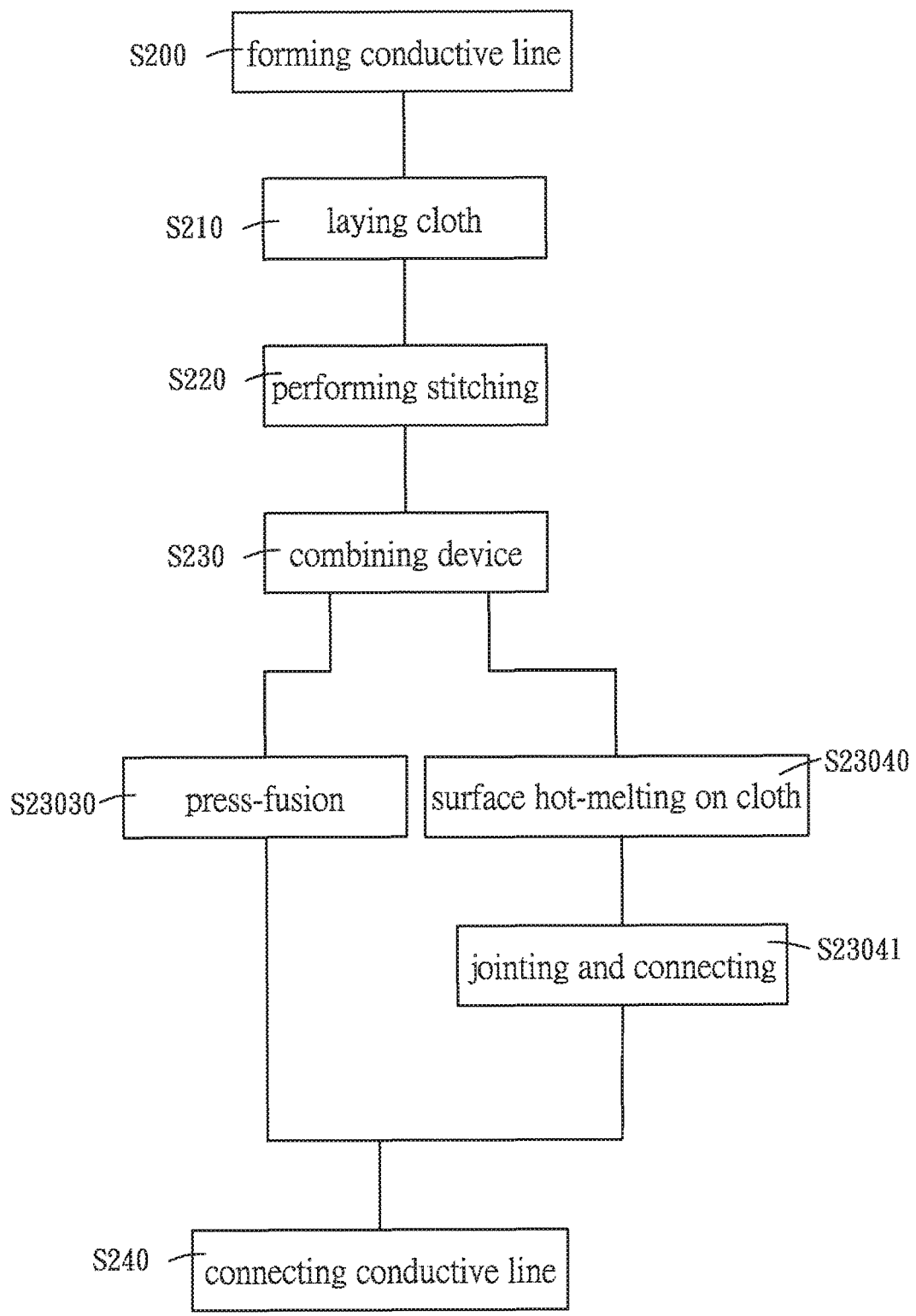
FIG. 12 is a flow chart illustrating the second method of the present invention that adopts a conductive piece.

Further, when the device involved in the above-described step of combining device S230 is a conductive piece 92, two types of combining step can be applied, wherein the conductive piece 92 comprises one of metal non-woven fabric, conductive rubber, conductive silicon rubber, and conductive films to possess excellent performance of transmission of data or power through metallic material or conductive material contained therein. The first type of the combining step (as shown in FIG. 12) is press-fusion 523030: wherein the conductive piece 92 and the stitched conductive line 60 are press-jointed by a manner of ultrasonic wave so that the conductive piece 92 and the conductive line 60 are fused and connected; and, in other words, one end of the conductive piece 92 is fixed on the conductive line 60 (as shown in FIG. 16) and a machine is operated to generate instantaneous high thermal energy for conducting press-jointing on the conductive piece 92 and the conductive line 60 simultaneously, which allows the protection layer 62 of the conductive line 60 located on the stitching area 71 to get melted due to the instantaneous high thermal energy and thus expose the internal metal line 61, and enables the exposed metal line 61 to form a fusion-connected condition with respect to the conductive piece 92 forming polarity engagement therefore. The above-described conductive piece 92, fusion-connected to the conductive line 60, is provided with a connection portion 921, and the said connection portion 921 is connectable with a suction-cup electrode 100 (as shown in FIG. 16), wherein the connection portion 921 and the suction-cup electrode 100 are respectively provided with mating male and female buckles or other applicable connection measures to allow the suction-cup electrode 100 to achieve a connected condition with the conductive piece 92 and the conductive line 60 through the connection portion 921. The suction-cup electrode 100 comprises a bottom portion 101, having an outer rim edge, which extends a circular part 102. Further, the circular part 102 has an upper end that forms an engagement surface 1021 for being positionable and attached to a human body skin to carry out detection of a physiological signal. The above-mentioned physiological signal can be any one of body temperature, heartbeat, pulse, and breath.

Further, the second type of combining step (as shown in FIG. 12) is surface hot-melting on cloth 523040: wherein a section of the conductive line 60 so stitched is subjected to surface hot melting on cloth to expose the metal line 61; and a section of the conductive line 60 is selected for removing the external protection layer 62 and exposing the internal metal line 61 (not shown) and a machine (such as a hot melting gun) that could generate instantaneous high temperature is used to have the that section selected to remove the protection layer 62 by melting. After the completion of the above-described surface hot-melting on cloth 523040, the next step performed is jointing and connecting 523041: wherein the conductive piece 92 is attached to or sewn to the location of the conductive line 60 where the metal line 61 is exposed to have the conductive piece 92 forming connection with the conductive line 60; and then, the protection layer 62 is removed from the conductive line 60 and the conductive piece 92 is coupled to the conductive line 60 by means of attaching or sewing (not shown) to have the conductive piece 92 forming electrical connection with the conductive line 60 of which the protection layer 62 is removed and the metal line 61 is exposed. The above-described conductive piece 92, fusion-connected to the conductive line 60, is provided with a connection portion 921, and the said connection portion 921 is connectable with a suction-cup electrode 100, wherein the connection portion 921 and the suction-cup electrode 100 are respectively provided with mating male and female buckles or other applicable connection measures to allow the suction-cup electrode 100 achieve a connected condition with the conductive piece 92 and the conductive line 60 through the connection portion 921. The suction-cup electrode 100 comprises a bottom portion 101, having an outer rim edge, which extends a circular part 102. Further, the circular part 102 has an upper end that forms an engagement surface 1021 for being positionable and attached to a human body skin to carry out detection of a physiological signal. The above-mentioned physiological signal can be any one of body temperature, heartbeat, pulse, and breath.

Further, after the completion of the above-described step of combining device S230, the next step performed (as shown in FIGS. 10, 11, and 12) is connecting conductive line S240: wherein the device 90 is set in connection with the conductive line 60 so stitched to allow the device 90 to perform transmission through the conductive line 60; and the device 90 (whether being an electrode plate 91 or a conductive piece 92) forms electrical connection with the conductive line 60 located on the stitching area 71 by means of the above-described method so that the conductive line 60 may transmit signals and data detected by the device 90 to an electronic apparatus (such as a smart phone, a smart tablet computer, a notebook computer, a desktop computer, and medical equipment) or cloud (not shown) for inspecting the result of data to take preventive medical treatment in advance.

With the detailed description provided above, those skilled in the art would realize that the present invention does achieve the above-described purpose and completely meet the regulations of the Patent Law, and the subject application is filed accordingly.

However, the above is provided for illustrating a preferred embodiment of the present invention only and should not be construed as constraining the scope of the present invention. Thus, simple and equivalent modifications and variations made according to the appended claims and the disclosure provided herein are considered within the scope of patent coverage of the present invention.

What is claimed is:

1. A conductive line stitching method, the method comprising:
   arranging a metal line in a protection layer to form a conductive line;
   positioning the conductive line on a stitching area of two stacked cloth sheets;
   performing stitching on the stitching area of the two stacked cloth sheets to locate the conductive line inside a stitching line;
   combining a detection device with the stitching line; and
   connecting the detection device to the conductive line.

2. The conductive line stitching method as claimed in claim 1, wherein the protection layer comprises an insulation layer formed of a material comprising polyvinyl chloride or a yarn line formed by spinning cotton, silk, hemp, animal hairs, or artificial fibers.

3. The conductive line stitching method as claimed in claim 1, wherein the detection device comprises an electrode plate, and the method further comprises:
   applying an ultrasonic wave to connect the electrode plate and the conductive line.

4. The conductive line stitching method as claimed in claim 1, wherein the detection device comprises an electrode plate, and the method further comprises:
   applying heat to a section of the conductive line located inside the stitching line to expose a portion of the metal line; and
   attaching the electrode plate to the conductive line where the metal line is exposed.

5. The conductive line stitching method as claimed in claim 1, wherein the detection device comprises a conductive piece including at least one of metal non-woven fabric, conductive rubber, conductive silicon rubber, and a conductive film, and the method further comprises:
   applying an ultrasonic wave to connect the conductive piece and the conductive line.

6. The conductive line stitching method as claimed in claim 1, wherein the detection device comprises a conductive piece including at least one of one of metal non-woven fabric, conductive rubber, conductive silicon rubber, and a conductive film, and the method further comprises:
   applying heat to a section of the conductive line located inside the stitching line to expose a portion of the metal line; and
   attaching the conductive piece to the conductive line where the metal line is exposed.

7. The conductive line stitching method as claimed in claim 5, wherein the conductive piece is further provided with a connection portion, the connection portion being a male/female buckle, the connection portion being further connected to a suction-cup electrode, the suction-cup electrode comprising a bottom portion, a wall body extending from an edge of the bottom portion, the wall body having an upper end forming an engagement surface.

8. The conductive line stitching method as claimed in claim 6, wherein the conductive piece is further provided with a connection portion, the connection portion being a male/female buckle, the connection portion being further connected to a suction-cup electrode, the suction-cup electrode comprising a bottom portion, a wall body extending from an edge of the bottom portion, the wall body having an upper end forming an engagement surface.

9. A conductive line stitching method, the method comprising:
   arranging a metal line in a protection layer to form a conductive line;

exposing edges of two stacked cloth sheets;

performing stitching of a stitching area adjacent to the exposed edges to locate the conductive line inside a stitching line;

combining a detection device with the stitching line; and connecting the detection device to the conductive line.

10. The conductive line stitching method as claimed in claim 9, wherein the protection layer comprises an insulation layer formed of a material comprising polyvinyl chloride or a yarn line formed by spinning cotton, silk, hemp, animal hairs, or artificial fibers.

11. The conductive line stitching method as claimed in claim 9, wherein the detection device comprises an electrode plate, and the method further comprises:

applying an ultrasonic wave to connect the electrode plate and the conductive line.

12. The conductive line stitching method as claimed in claim 9, wherein the detection device comprises an electrode plate, and the method further comprises:

applying heat to a section of the conductive line to expose the metal line; and attaching the electrode plate to the conductive line where the metal line is exposed.

13. The conductive line stitching method as claimed in claim 9, wherein the detection device comprises a conductive piece including at least one of metal non-woven fabric, conductive rubber, conductive silicon rubber, and a conductive film, and the method further comprises:

applying an ultrasonic wave to connect the conductive piece and the conductive line.

14. The conductive line stitching method as claimed in claim 9, wherein the detection device comprises a conductive piece including at least one of metal non-woven fabric, conductive rubber, conductive silicon rubber, and a conductive film, and the method further comprises:

applying heat to a section of the conductive line located inside the stitching line to expose a portion of the metal line; and attaching the conductive piece to the conductive line where the metal line is exposed.

15. The conductive line stitching method as claimed in claim 13, wherein the conductive piece is further provided with a connection portion, the connection portion being a male/female buckle, the connection portion being further connected to a suction-cup electrode, the suction-cup electrode comprising a bottom portion, a wall body extending from an edge of the bottom portion, the wall body having an upper end forming an engagement surface.

16. The conductive line stitching method as claimed in claim 14, wherein the conductive piece is further provided with a connection portion, the connection portion being a male/female buckle, the connection portion being further connected to a suction-cup electrode, the suction-cup electrode comprising a bottom portion, a wall body extending from an edge of the bottom portion, the wall body having an upper end forming an engagement surface.

* * * * *